United States Patent [19]

Goldberg et al.

[11] Patent Number: 4,992,537

[45] Date of Patent: Feb. 12, 1991

[54] CDNA ENCODING 92-KDA TYPE IV COLLAGENASE

[75] Inventors: Gregory I. Goldberg; Arthur Z. Eisen, both of St. Louis, Mo.

[73] Assignee: Washington University, St. Louis, Mo.

[21] Appl. No.: 352,078

[22] Filed: May 15, 1989

[51] Int. Cl.$^5$ ............................................. C12N 15/00
[52] U.S. Cl. ........................................ 536/27; 435/69.1; 435/172.3; 530/219; 530/226
[58] Field of Search .............. 536/27; 435/69.1, 172.3; 530/219, 226

[56] References Cited

U.S. PATENT DOCUMENTS 4,677,058 6/1987 Tryggvason ........................... 435/7
4,772,557 9/1988 Eisen et al. ........................... 435/320

OTHER PUBLICATIONS

Kemp, D. J. and Conman, A. F., 1981 PNAS 78(7), 4520–4524.
Skalka, A. and Shapiro, L., 1976 Gene 1:65–79.
Seltzer et al., J. Biol. Chem. 256, 4662–4668 (1981).
Sopata, Biochim. Biophys. Acta 717, 26–31 (1982).
Seltzer et al., J. Chromatog. 326, 147–155 (1985).
Murphy et al., Biochim. Biophys. Acta 831, 49–58 (1985).
Hibbs et al., J. Biol. Chem. 260, 2493–2500 (1985).
Goldberg et al., J. Biol. Chem. 261, 6600–6605 (1986).
Yoakum et al., Science 227, 1174–1179 (1985).
Wilhelm et al., Proc. Natl., Acad. Sci. U.S.A. 84, 6725–6729 (1987).
Collier et al., J. Biol. Chem. 263, 6579–6587 (1988).

Primary Examiner—Richard A. Schwartz
Attorney, Agent, or Firm—Scott J. Meyer; James W. Williams, Jr.

[57] ABSTRACT

A novel 92-kDa type IV collagenase has been purified to homogeneity from SV-40 transformed fetal lung fibroblasts, its primary structure determined and characterized and a cDNA clone representing the full size protein has been developed.

1 Claim, 12 Drawing Sheets

```
AGACACCTCTGCCCTCACCATGAGCCTCTGGCAGCCCCTGGTCCTGGTGC   50
                  M   S   L   W   Q   P   L   V   L   V
                              *
TCCTGGTGCTGGGCTGCTGCTTTGCTGCCCCAGACAGCGCCAGTCCACC  100
 L   L   V   L   G   C   C   F   A   A   P   R   Q   R   Q   S   T

CTTGTGCTCTTCCCTGGAGACCTGAGAACCAATCTCACCGACAGGCAGCT  150
 L   V   L   D   P   F   S   L   E   R   N   L   T   D   R   Q   L

GGCAGAGGAATACCTGTACCGCTATGGTTACACTCGGGTGGCAGAGATGC  200
 A   E   E   Y   L   Y   R   Y   G   Y   T   R   V   A   E   M

GTGGAGAGTCGAAATCTCTGGGGCCTGCGCTGCTGCTTCTCCAGAAGCAA  250
 R   G   E   S   K   S   L   G   P   A   L   L   L   L   Q   K   Q
                                                              *
CTGTCCCTGCCCGAGACCGGTGAGCTGGATAGCGCCACGCTGAAGGCCAT  300
 L   S   L   P   E   T   G   E   L   D   S   A   T   L   K   A   M

GCGAACCCCACGGTGCGGGGTCCCAGACCTGGGCAGATTCCAAACCTTTG  350
   R   T   P   R   C   G   V   P   D   L   G   R   F   Q   T   F

AGGGCGACCTCAAGTGGCACCACCACAACATCACCTATTGGATCCAAAAC  400
 E   G   D   L   K   W   H   H   H   N   I   T   Y   W   I   Q   N

TACTCGGAAGACTTGCCGCGGGCGGTGATTGACGACGCCTTTGCCCGCGC  450
   Y   S   E   D   L   P   R   A   V   I   D   D   A   F   A   R   A

CTTCGCACTGTGGAGCGCGGTGACGCCGCTCACCTTCACTCGCGTGTACA  500
 F   A   L   W   S   A   V   T   P   L   T   F   T   R   V   Y

GCCGGGACGCAGACATCGTCATCCAGTTGGGTGTCGCGGAGCACGGAGAC  550
 S   R   V   A   D   I   V   I   Q   F   G   B   A   E   H   G   D

GGGTATCCCTTCGACGGGAAGGACGGGCTCCTGGCACACGCCTTTCCTCC  600
 G   Y   P   F   D   G   K   D   G   L   L   A   H   A   F   P   P

TGGCCCCGGCATTCAGGGAGACGCCCATTTCGACGATGACGAGTTGTGGT  650
   G   P   G   I   Q   G   D   A   H   F   D   D   D   E   L   W

CCCTGGGCAAGGGCGTCGTGGTTCCAACTCGGTTTGGAAACGCAGATGGC  700
 S   L   G   K   G   V   V   V   P   T   R   F   G   N   A   D   G

GCGGCCTGCCACTTCCCCTTCATCTTCGAGGGCCGCTCCTACTCTGCCTG  750
 A   A   C   H   F   P   F   I   F   E   G   R   S   Y   S   A   C

CACCACCGACGGTCGCTCCGACGGCTTGCCCTGGTGCAGTACCACGGCCA  800
   T   T   D   G   R   S   D   G   L   P   W   C   S   T   T   A

ACTACGACACCGACGACCGGTTTGGCTTCTGCCCCAGCGAGAGACTCTAC  850
 N   Y   D   T   D   D   R   F   G   F   C   P   S   E   R   L   Y

ACCCGGGACGGCAATGCTGATGGGAAACCCTGCCAGTTTCCATTCATCTT  900
   T   R   D   G   N   A   D   G   K   P   C   Q   F   P   F   I   F
```

| Peptide | | AA position |
|---|---|---|
| TP12 | VYTGASVLGPR | 589-600 |
| TP16 | PQGPFLIADKXPALP | 550-564 |
| V7 | XDRMFPG | 600-606 |
| NP | APRQRQSTLVLFPGDLRT | 20-38 |
| NA-1 | MRTPR(Q)GVPDL | 93-103 |
| NA-2 | LL(G)QKXLSLPE | 72-82 |

CN 2209    CAGGTCGCCAGGGAACAGCACCAGGGTIG/CA/TCTGICG/TCTGIC/GGGGGGC
           Nucleotides 77-124

```
AGACACCTCTGCCCTCACCATGAGCCTCTGGCAGCCCCTGGTCCTGGTGC  50
                    M  S  L  W  Q  P  L  V  L  V
                              *
TCCTGGTGCTGGGCTGCTGCTTTGCTGCCCCCAGACAGCGCCAGTCCACC  100
 L  L  V  L  G  C  C  F  A  A  P  R  Q  R  Q  S  T

CTTGTGCTCTTCCCTGGAGACCTGAGAACCAATCTCACCGACAGGCAGCT  150
 L  V  L  D  P  F  S  L  E  R  N  L  T  D  R  Q  L

GGCAGAGGAATACCTGTACCGCTATGGTTACACTCGGGTGGCAGAGATGC  200
  A  E  E  Y  L  Y  R  Y  G  Y  T  R  V  A  E  M

GTGGAGAGTCGAAATCTCTGGGGCCTGCGCTGCTGCTTCTCCAGAAGCAA  250
 R  G  E  S  K  S  L  G  P  A  L  L  L  Q  K  Q
                                              *
CTGTCCCTGCCCGAGACCGGTGAGCTGGATAGCGCCACGCTGAAGGCCAT  300
 L  S  L  P  E  T  G  E  L  D  S  A  T  L  K  A  M

GCGAACCCCACGGTGCGGGGTCCCAGACCTGGGCAGATTCCAAACCTTTG  350
 R  T  P  R  C  G  V  P  D  L  G  R  F  Q  T  F

AGGGCGACCTCAAGTGGCACCACCACAACATCACCTATTGGATCCAAAAC  400
 E  G  D  L  K  W  H  H  H  N  I  T  Y  W  I  Q  N

TACTCGGAAGACTTGCCGCGGGCGGTGATTGACGACGCCTTTGCCCGCGC  450
 Y  S  E  D  L  P  R  A  V  I  D  D  A  F  A  R  A

CTTCGCACTGTGGAGCGCGGTGACGCCGCTCACCTTCACTCGCGTGTACA  500
 F  A  L  W  S  A  V  T  P  L  T  F  T  R  V  Y

GCCGGGACGCAGACATCGTCATCCAGTTGGGTGTCGCGGAGCACGGAGAC  550
 S  R  V  A  D  I  V  I  Q  F  G  B  A  E  H  G  D

GGGTATCCCTTCGACGGGAAGGACGGGCTCCTGGCACACGCCTTTCCTCC  600
 G  Y  P  F  D  G  K  D  G  L  L  A  H  A  F  P  P

TGGCCCCGGCATTCAGGGAGACGCCCATTTCGACGATGACGAGTTGTGGT  650
 G  P  G  I  Q  G  D  A  H  F  D  D  D  E  L  W

CCCTGGGCAAGGGCGTCGTGGTTCCAACTCGGTTTGGAAACGCAGATGGC  700
 S  L  G  K  G  V  V  V  P  T  R  F  G  N  A  D  G

GCGGCCTGCCACTTCCCCTTCATCTTCGAGGGCCGCTCCTACTCTGCCTG  750
 A  A  C  H  F  P  F  I  F  E  G  R  S  Y  S  A  C

CACCACCGACGGTCGCTCCGACGGCTTGCCCTGGTGCAGTACCACGGCCA  800
 T  T  D  G  R  S  D  G  L  P  W  C  S  T  T  A

ACTACGACACCGACGACCGGTTTGGCTTCTGCCCCAGCGAGAGACTCTAC  850
 N  Y  D  T  D  D  R  F  G  F  C  P  S  E  R  L  Y

ACCCGGGACGGCAATGCTGATGGGAAACCCTGCCAGTTTCCATTCATCTT  900
 T  R  D  G  N  A  D  G  K  P  C  Q  F  P  F  I  F
```

FIG. 3

```
CCAAGGCCAATCCTACTCCGCCTGCACCACGGACGGTCGCTCCGACGGCT    950
  Q  G  Q  S  Y  S  A  C  T  T  D  G  R  S  D  G

ACCGCTGGTGCGCCACCACCGCCAACTACGACCGGGACAAGCTCTTCGGC   1000
  Y  R  W  C  A  T  T  A  N  Y  D  R  D  K  L  F  G

TTCTGCCCGACCCGAGCTGACTCGACGGTGATGGGGGGCAACTCGGCGGG   1050
  F  C  P  T  R  A  D  S  T  V  M  G  G  N  S  A  G

GGAGCTGTGCGTCTTCCCCTTCACTTTCCTGGGTAAGGAGTACTCGACCT   1100
  E  L  C  V  F  P  F  T  F  L  G  K  E  Y  S  T

GTACCAGCGAGGGCGCGGAGATGGGCGCCTCTGGTGCGCTACCACCTCG    1150
  C  T  S  E  G  R  G  D  G  R  L  W  C  A  T  T  S

AACTTTGACAGCGACAAGAAGTGGGGCTTCTGCCCGGACCAAGGATACAG   1200
  N  F  D  S  D  K  K  W  G  F  C  P  D  Q  G  Y  S

TTTGTTCCTCGTGGCGGCGCATGAGTTCGGCCACGCGCTGGGCTTAGATC   1250
  L  F  L  V  A  A  H  E  F  G  H  A  L  G  L  D

ATTCCTCAGTGCCGGAGGCGCTCATGTACCCTATGTACCGCTTCACTGAG   1300
  H  S  S  V  P  E  A  L  M  Y  P  M  Y  R  F  T  E

GGGCCCCCCTTGCATAAGGACGACGTGAATGGCATCCGGCACCTCTATGG   1350
  G  P  P  L  H  K  D  D  V  N  G  I  R  H  L  Y  G

TCCTCGCCCTGAACCTGAGCCACGGCCTCCAACCACCACCACACCGCAGC   1400
  P  R  P  E  P  E  P  R  P  P  T  T  T  T  P  Q

CCACGGCTCCCCCGACGGTCTGCCCCACCGGACCCCCCACTGTCCACCCC   1450
  P  T  A  P  P  T  V  C  P  T  G  P  P  T  V  H  P

TCAGAGCGCCCCACAGCTGGCCCCACAGGTCCCCCCTCAGCTGGCCCCAC   1500
  S  E  R  P  T  A  G  P  T  G  P  P  S  A  G  P  T

AGGTCCCCCCACTGCTGGCCCTTCTACGGCCACTACTGTGCCTTTGAGTC   1550
  G  P  P  T  A  G  P  S  T  A  T  T  V  P  L  S

CGGTGGACGATGCCTGCAACGTGAACATCTTCGACGCCATCGCGGAGATT   1600
  P  V  D  D  A  C  N  V  N  I  F  D  A  I  A  E  I

GGGAACCAGCTGTATTTGTTCAAGGATGGGAAGTACTGGCGATTCTCTGA   1650
  G  N  Q  L  Y  L  F  K  D  G  K  Y  W  R  F  S  E

GGGCAGGGGGAGCCGGCCGCAGGGCCCCTTCCTTATCGCCGACAAGTGGC   1700
  G  R  G  S  R  P  Q  G  P  F  L  I  A  D  K  W

CCGCGCTGCCCCGCAAGCTGGACTCGGTCTTTGAGGAGCCGCTCTCCAAG   1750
  P  A  L  P  R  K  L  D  S  V  F  E  E  P  L  S  K

AAGCTTTTCTTCTTCTCTGGGCGCCAGGTGTGGGTGTACACAGGCGCGTC   1800
  K  L  F  F  F  S  G  R  Q  V  W  V  Y  T  G  A  S
```

FIG. 3A

```
GGTGCTGGGCCCGAGGCGTCTGGACAAGCTGGGCCTGGGAGCCGACGTGG    1850
  V  L  G  P  R  R  L  D  K  L  G  L  G  A  D  V

CCCAGGTGACCGGGGCCCTCCGGAGTGGCAGGGGGAAGATGCTGCTGTTC    1900
 A  Q  V  T  G  A  L  R  S  G  R  G  K  M  L  L  F

AGCGGGCGGCGCCTCTGGAGGTTCGACGTGAAGGCGCAGATGGTGGATCC    1950
  S  G  R  R  L  W  R  F  D  V  K  A  Q  M  V  D  P

CCGGAGCGCCAGCGAGGTGGACCGGATGTTCCCCGGGGTGCCTTTGGACA    2000
   R  S  A  S  E  V  D  R  M  F  P  G  V  P  L  D

CGCACGACGTCTTCCAGTACCGAGAGAAAGCCTATTTCTGCCAGGACCGC    2050
 T  H  D  V  F  Q  Y  R  E  K  A  Y  F  C  Q  D  R

TTCTACTGGCGCGTGAGTTCCCGGAGTGAGTTGAACCAGGTGGACCAAGT    2100
  F  Y  W  R  V  S  S  R  S  E  L  N  Q  V  D  Q  V

GGGCTACGTGACCTATGACATCCTGCAGTGCCCTGAGGACTAGGGCTCCC    2150
   G  Y  V  T  Y  D  I  L  Q  C  P  E  D

GTCCTGCTTTGCAGTGCCATGTAAATCCCCACTGGGACCAACCCTGGGGA    2200

AGGAGCCAGTTTGCCGGATACAAACTGGTATTCTGTTCTGGAGGAAAGGG    2250

AGGAGTGGAGGTGGGCTGGGCCCTCTCTTCTCACCTTTGTTTTTTGTTGG    2300

AGTGTTTCTAATAAACTTGGATTCTCTAACCTTT                   2334
```

```
MSLVQPLVLVLLVLGCCFAAPRQRQSTLVLFPGDLRTN       44
MEALMARGALTGPLRA CL   LLSHAAAAP PIIK    .VAP

LTDRQLAEEYLYRYGYTRVAEMRGESKSLGPALLLLQKQLSLPE  88
K  KE  VQ  NT.F GCPK  SCNLFVLKDT. KKM  FFG Q

TGELDSATLKAMRTPRCGVPDLGRFQTFEGDLKWHHHNITYWIQ 132
   D  QN IET  K     N  VANYNF PRKP  DKNQ  R I

NYSEDLPRAVIDDAFARAFALWSAVTPLTFTRVYSRDADIVIQF 176
G TP  DPETV       QV      R S  IHDGE   M N

GVAEHGDGYPFDGKDGLLAHAFPPGPGIQGDAHFDDDELWSLGK 220
RW              A   T VG S        T   E

GVVVPTRFGNADGAACHFPFIFEGRSYSACTTDGRSDGLPWCST 264
Q  RVKY    EY K   L N KE NS  DT     FL

TANYDTDDRFGFCPSERLYTRDGNADGKPCQFPFIFQGQSYSAC 308
Y FEK  GKY    H A F MG · E Q    K   R   T  DS

TTDGRSDGYRWCATTANYDRDKLFGFCPTRADSTVMGGNSAGEL 396
   E   T     G  ED      KY    ET M   .    E AP

CVFPPTFLGKEYSTCTSEGRGDGRLWCATTSNFDSDKKWGFCPD 396
        NK ES   A  S   KM       A Y D R

QGYSLFLVAAHEFGHALGLDHSSVPEALMYPMYRFTEGPPLHKD 440
          M  E   QD G   A I TY KNFR SQ

DVNGIRHLYGPRPEPEPRPPTTTTPQPTAPPTVCPTGPPTVHPS 484
IK  QE     ......................
     +   GP G VG ...SGKEGN GPLG L   GVRG

ERPTAGPTGPP.SAGPTGPPTAGPSTATTVPLSPVDD.....AC 528
.................ASPDIDLG G TPTLGPVTPEICK
.VGE    E   GEP  P    +       ALPHA2(V)

NVNIFDAIAEIGNQLYLFKDGKYWRFSEGRGSRPQGPFLIADKW 572
QDIV  G  Q RGEIFF   RFI   TVTP .DK M  L V TF

PALPRKLDSVFEEPLSKKLFFFSGRQVWVYTGASVL....GPRR 616
 E   E I A Y A QEE AV   A NEY I .S  T ERGYPKPL

LDKLGLGADVAQVTGALRSGR.GKMLLFSGRRLWRFDVKAQMVD 660
TS.    PP   QR DA FNWSKNK  TYIFA  DKF  YNEVKKKM

PRSASEVDRMFPGVPLDTHDVFQYREKA..YFCQDRFYWRVSSR 704
 GFPKLIADAWNAI DNLDA VDLQGGGHS  FKGAY LKLENQ

SELNQVDQVGYVTYDILQCPED*      TYPE IV-92kDa    725
. KS KF. SIKS W G *           TYPE IV-72kDa
```

CDNA ENCODING 92-KDA TYPE IV COLLAGENASE

BACKGROUND OF THE INVENTION

This invention relates to a novel 92-kDA type IV collagenase and a cDNA clone representing the full size protein.

Resident cells of tissues are capable of secreting an array of enzymes initiating the degradation of the surrounding macromolecules of extracellular matrix (ECM), which presumably contributes to the initial steps of tissue remodeling during morphogenesis, wound healing, angiogenesis and tumor invasion. Several of the metalloproteases of this class have been shown to be structurally related and comprise a novel secreted protease gene family, which includes, among other things, collagenase, stromelysin, and a 72-kDA type IV collagenase. The expression of genes coding for these enzymes is cell-type specific, and is regulated by growth factors, oncogenes, mediators of inflammation and tumor promoters. The extracellular activity of these enzymes is modulated by proenzyme activation, interaction with the specific tissue inhibitor of metalloprotease (TIMP), and microenvironmental factors such as tissue localization.

The ECM metalloproteases are secreted as zymogens which undergo extracellular activation. One possible pathway of activation of interstitial collagenase involves a cascade of proteolytic events in which processing of the amino-terminal portion of the enzyme by plasmin results in removal of 84 amino acid residues. A second step requires the presence of plasmin activated stromelysin, which removes approximately 15 residues from the carboxy end of the molecule, resulting in the fully activated enzyme. Interstitial collagenase once activated can form an enzyme inhibitor complex with TIMP. However, no complex formation between the latent procollagenase and TIMP occurs.

The present inventors have previously disclosed in copending application Ser. No. 07/93,421, filed Sept. 4, 1987, that human bronchial epithelial cells secrete a 72-kDa type IV collagenase in response to transformation with the H-ras oncogene. See also Collier et al., J. Biol. Chem. 263, 6579–6587 (1988). The same enzyme is secreted by a variety of tumor cells as well as by normal human skin fibroblasts.

BRIEF DESCRIPTION OF THE INVENTION

In accordance with the present invention, a novel 92-kilodalton (kDa) type IV collagenase has been purified to homogeneity from SV-40 transformed fetal lung fibroblasts and from U-937 monocytic leukemia cells, and its primary structure has been determined and characterized.

The pre-proenzyme is synthesized as a polypeptide of predicted $M_r$ 78,426 containing a 19 amino-acid-long signal peptide and secreted as a single 92-kDa glycosylated proenzyme. The purified proenzyme complexes non-covalently with the tissue inhibitor of metalloproteases (TIMP) and can be activated by organomercurials Activation with PMC results in removal of 73 amino acids from the NH$_2$-terminus of the proenzyme, yielding an active form capable of digesting native types IV and V collagen. The in vitro substrate specificity of the enzyme using these substrates was indistinguishable from that of 72-kDa type IV collagenase.

The novel 92-kDa type IV collagenase of the present invention consists of five domains; the amino-terminal and Zinc-binding domains shared by all members of the secreted metalloprotease gene family, the collagen binding fibronectin-like domain present only in the 72-kDa type IV collagenase, a carboxyl-terminal hemopexin-like domain shared by all known enzymes of this family with the exception of PUMP-1, and a unique 54 amino acid long proline-rich domain homologous to the alpha2 chain of type V collagen. This 54 amino acid domain is not found in the 72-kDa type IV collagenase or in other members of the secreted ECM metalloprotease gene family.

Also unlike the 72-kDa type IV collagenase, expression of the 92-kDa enzyme is induced by epidermal growth factor (EGF), interleukin 1, and the tumor promoter, 12-0-tetradecanoylphorbol acetate (TPA). Enzyme secretion is also increased with the differentiation of the blood monocytes into alveolar macrophages.

Further unlike the 72-kDa enzyme, the 92-kDa type IV collagenase contains three potential N-glycosylation sites and is completely glycosylated. The specific role of glycosylation in the metabolism of the secreted metalloproteases, however, is not yet understood. Both interstitial collagenase and stromelysin are partially glycosylated without any noticeable effect of glycosylation on the behavior of the purified enzyme in vitro. However, it is known, in general, that the carbohydrate structure of a glycoprotein can have a significant effect upon its biological activity. That is, the oligosaccharides can affect the protein's antigenicity, stability, solubility and tertiary structure. The carbohydrate sidechains also can influence the protein's half-life and target it to receptors on the appropriate cells. The carbohydrate residues can affect both inter- and intracellular recognition. The sugar groups thus can control the relative effectiveness of a therapeutic protein when administered to a patient. These and other such functions of the carbohydrate moiety of glycoproteins are discussed, for example, by Delente, Trends in Biotech. 3(9), 218 (1985); van Brunt, Bio/Technology 4, 835–839 (1986); and Taunton-Rigby, Biotech USA 1988, Proc. Conf. San Francisco, Nov. 14–16, 1988, pp. 168–176.

In accordance with another aspect of the present invention, a cDNA clone representing the full size 92-kDa type V collagenase has been developed. The cDNA insert in this clone, p92174.1, contains 2334 bp, excluding the poly AT and the poly GC tails and represents the mRNA encoding the 92-kDa preproenzyme. The sequence contains a 19 bp 5' untranslated region followed by an AUG initiating methionine codon and an open reading frame with coding capacity for 707 amino acid long preproenzyme of predicted $M_r=78,426$. The 193 nucleotides long 3' untranslated region contains the putative poly A addition site 19 bases upstream from the 3' end of the RNA. The first 19 amino acids of the predicted sequence constitute a hydrophobic signal peptide followed by the start of the mature secreted protein at APRQR, as determined by amino acid sequence analysis.

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention taken in conjunction with the appended drawings, in which:

FIG. 3 shows the nucleotide sequence of the human 92 kDa type IV collagenase cDNA. The sequence was determined on both strands as described hereinafter under "Materials and Methods". The predicted aminoacid sequence of the enzyme is shown under the DNA sequence. The aminoterminus of the mature and PMC activated enzyme is indicated by an asterisk. The potential glycosylation sites and the putative poly A addition signal are underlined.

FIG. 4 shows the Northern Blot analysis of 92-kDa type IV collagenase expression in normal and transformed cells. Cells were treated for 20 h with active and inactive diasteromers of indolactam V, V(−) and V(+), epidermal growth factor (EGF), and interleukin 1B (IL-1), in serum-free medium as described hereinafter under "Materials and Methods". Total RNA (15 µg) was isolated, electrophoresed in a formaldehyde gel and transferred to a zeta probe membrane. The blot was hybridized using a 1.2 kb Sma fragment labeled with $^{32}$P using random priming. 28S and 18S represent the ribosomal RNA markers. The blot was exposed for 48 h.

FIG. 5 shows the N- and O-linked glycosylation of the 92-kDa type IV collagenase. Samples of purified (U937 cells) type IV procollagenase (2 µg) were incubated with either endoglycosidase H (lane 2), N-glycanase (lane 3), O-glycanase (lane 4), or in buffer only (lanes 1 and 5) for 16 h at 37° C. and subjected to immunoblot analysis. Alternatively, TPA-differentiated U-937 cells were biosynthetically labeled in the presence (lane /) or absence (lane of 0.5 µg/ml of tunicamycin for 16 h and of conditioned medium were immunoprecipitated using 92-kDa monospecific antiserum as described hereafter under "Materials and Methods."

FIG. 6 shows the structural relationship between human 72- and 92-kDa type IV collagenases. Top line, amino acid sequence of the 92-kDa type IV collagenase as in FIG. 3. Second line, human 72-kDa type IV collagenase. The sequence of the signal peptide of this protein was reconstructed from the DNA sequence of the genomic clone of the enzyme. The lines designated with +represent the partial sequence of the alpha2 chain of type V collagen (positions 961-1011 [Weil et al., Nuc. Acids Res. 15, 181-198 (1987)], homologous to the collagen like domain of the 92-kDa type IV collagenase. Deletions are represented by—. Only the amino acid residues that differ from the top line are indicated.

FIG. 7 shows the mosaic structure of the secreted ECM metalloproteases. The bars represent domain of the proteins as indicated. The domains are aligned according to the amino acid sequence homology alignment.

FIG. 8 shows the PMC activation of TIMP 92-kDa type IV collagenase complex. 2 µg of the enzyme purified from U-937 cells (lane 1) or SV40 transformed human lung fibroblast (lane 2) were electrophoresed and stained with silver. 0.5 µg of the enzyme was transferred on to a filter and developed with anti-TIMP antibody (lane 3) or anti-92-kDa antibody before (lane or after (lane 5) activation with 0.5 mM PMC for 16h. 10 ng of the same preparations were analyzed on a gelatin zymogram and developed for 2h (lane 6, before activation; lane 7, after activation).

(A) Gel-filtration chromatography. 60 µg of gelatin SEPHAROSE ® purified 92-kDa enzyme from U-937 cells was chromatographed on a AcA-44 column in a buffer containing 1 M NaCl. Lane 1 represents 2 µg of gelatin Sepharose purified enzyme starting material; lanes 2-7 represent various portions from the gel-filtrati profile.

(B) Gelatin Sepharose purified enzyme was chromatographed on a column of phenyl-Sepharose as described hereinafter under "Materials and Methods". Lane 1 represents 2 µg of starting material, lanes 2-6 represent fractions from the stepwise elution of the column using 1.0, 0.5, 0.2, 0.1, and 0.5 M NaCl containing 50% v/v ethylene glycol, respectively.

(C) Gel filtration chromatography in the presence of 0.19% NaDodSO$_4$. 60 µg of gelatin Sepharose purified enzyme was applied to an AcA-44 column in a buffer containing 0.19% NaDodSO$_4$. Lanes 1-7 represent fractions from the gel filtration profile.

Standard biochemical nomenclature is used herein in which the nucleotide bases of DNA or oligonucleotides are designated as adenine (A); thymine (T); guanine (G); and cytosine (C). Amino acids are shown either by three letters or one letter abbreviations as follows:

| Abbreviated Designation | | Amino Acid |
| --- | --- | --- |
| A | Ala | Alanine |
| C | Cys | Cysteine |
| D | Asp | Aspartic acid |
| E | Glu | Glutamic acid |
| F | Phe | Phenylalanine |
| G | Gly | Glycine |
| H | His | Histidine |
| I | Ile | Isoleucine |

-continued

| Abbreviated Designation | | Amino Acid |
|---|---|---|
| K | Lys | Lysine |
| L | Leu | Leucine |
| M | Met | Methionine |
| N | Asn | Asparagine |
| P | Pro | Proline |
| Q | Gln | Glutamine |
| R | Arg | Arginine |
| S | Ser | Serine |
| T | Thr | Threonine |
| V | Val | Valine |
| W | Trp | Tryptophan |
| Y | Tyr | Tyrosine |

In order to illustrate specific preferred embodiments of the invention in greater detail, the following exemplary laboratory preparative work was carried out.

EXAMPLE 1

Materials and Methods

Cell CuLture

SV-40 transformed fetal lung fibroblasts and the parental human diploid cell line IMR-90 (from the NIH Institute for Aging, Bethesda) were cultured in Eagle's minimum essential medium containing 29 μg/ml of glutamine and 10% fetal calf serum. The monocytic leukemia strain U-937 (from the Washington University School of Medicine Cancer Center) was cultured in RPMI-1640 containing 5% fetal calf serum. The fibrosarcoma cell strain HT-1080 was obtained from the American Type Culture Collection. The cell lines IMR-90, U-937 and HT-1080 are all available from the American Type Culture Collection, Rockville, Maryland, in unrestricted deposits under accession numbers ATCC CCL 186, ATCC CRL 1593, and ATCC CCL 121, respectively. Serum-free conditioned medium from human alveolar macrophages ($1 \times 10^6$ cells/ml) and 12-0-tetradecanoylphorbol acetate (TPA)-treated polymorphonuclear leukocytes ($1 \times 10^6$ cells/ml) Hibbs et al., *J. Biol. Chem.* 260, 2493-2500 (1985)]from Drs. Howard Welgus and Edward Campbell, Jewish Hospital, St. Louis). Conditioned medium from TPA-treated human skin keratinocytes ($3 \times 10^6$ cells/ml) was obtained from Dr. Alice Pentland, Washington University, St. Louis).

U-937 cells ($2 \times 10^6$ cells/ml) were treated with TPA (50 ng/ml) in Dulbeccos modified Eagle's/F-12 medium containing 0.1% fetal serum for 24-48 hours. TPA-differentiated U-937 cells were biosynthetically labeled with $^{35}$S-methionine (1100 Ci/mmol, Amersham) by conventional methodology as described by Wilhelm et al., *Proc. Natl. Acad. Sci. USA* 83, 3756-3760 (1986) and Wilhelm et al., *Ibid.* 84, 6725-6729 (1987), in the presence or absence of 0.5 μg/ml of tunicamycin. Cultures were treated with Indolactam V(−) and (+) (L.C. Services) dissolved in dimethylsulfoxide (DMSO) at a final concentration of 200 ng/ml for 24 hours. SV-40 transformed IMR-90 cells were grown to 80% confluence and treated with either interleukin-lB (Ciston) at 5 units/ml or epidermal growth factor (EGF) (Collaborative Research) at 20 ng/ml in serum-free medium for 20-24 h.

Enzyme Purification

The 92-kDa metalloprotease was purified from conditioned medium of SV-40 transformed fibroblasts or TPA-differentiated U-937 cells using a three-step procedure. Serum-free medium was adjusted to 0.01 M Tris-HCl, pH 7.5, and applied to a $2.5 \times 10$ cm column of reactive red Agarose (Sigma) equilibrated in 0.02 M Tris-HCl, pH 7.5, containing 0.005 M $CaCl_2$ (Tris/CaCl₂ Buffer) and 0.15 M NaCl. The enzyme was eluted from the column using 0.15 to 2.0 M NaCl linear gradient in Tris/CaCl₂ Buffer and fractions were assayed by conventional gelatin zymography as described by Heussen and Dowdle, *Anal. Biochem.* 102, 196 (1980).

Fractions containing 92-kDa gelatinolytic activity were pooled, adjusted to 0.5 M NaCl₂ and 0.01% BRIG ®-35 detergent and chromatographed on a 1.0 $\times 10$ cm column of gelatin-Sepharose ® (Sigma) by conventional techniques as previously described by Collier et al., *J. Biol. Chem.* 263, 6579-6587 (1988) and Hibbs et al., *Ibid.* 260, 2493-2500 1985), except the enzyme was eluted using a 0-10% DMSO gradient. Gelatin-Sepharose purified enzyme was dialyzed into 0.005 M Tris-HCl, pH 7.5, buffer containing 0.0001 M $CaCl_2$ and 0.005% Brij-35 and stored at $-80°$ C. This preparation was passed over an AcA-44 (IBS Biotechnics) column ($0.5 \times 90$ cm) and equilibrated in Tris/CaCl₂ buffer containing 1.0 M NaCl and 0.01% Brij-35.

Gel-filtration was also performed in 0.02 M Tris-HCl, pH 7.5, containing either 2.0 M urea or 0.1% NaDodSO₄ in an effort to separate the proenzyme and TIMP complex. Hydrophobic interaction chromatography was carried out by adjusting this preparation to 4.0 NaCl, and applying the sample to a $0.5 \times 2.0$ cm column of phenyl-Sepharose (Pharmacia). The column was eluted stepwise using 1.0, 0.5, 0.2, 0.1 M NaCl and 0.5 M NaCl containing 50% ethylene glycol in Tris/CaCl₂ buffer.

Antibody Preparation

Monospecific antiserum was prepared using NaDodSO₄ gel slices containing 50–75 μg of protein emulsified in Freund's complete adjuvant and injected into multiple sites at biweekly intervals for up to 2 months. Electrophoretic (Western) blotting was performed as described by Wilhelm et al., *Proc. Natl. Acad. Sci. USA* 83, 3756-3760 (1986), except that the nitrocellulose blots were developed using a 1:250 dilution of primary antiserum and a horseradish peroxidase ABC kit (Vector Laboratories) as described by the manufacturer.

Sequence Analysis

The gelatin-Sepharose purified enzyme was subjected to reverse-phase HPLC using an Applied Biosystems 130 A column ($2.1 \times 30$ mm) equilibrated in 0.07% trifluoroacetic acid. The column was developed with a linear gradient of 0–70% acetonitrile in 0.07% trifluoroacetic acid. HPLC purified U-937 92-kDa metalloprotease (10 μg) was digested with either TPCK-trypsin (Worthington) as described by Collier et al., *J. Biol. Chem.* 263, 6579-6587 (1988), or V-8 Staph aureus protease (Pierce) in sodium phosphate buffer, pH 7.8, at a 1:20 w/w ratio for 20h at 37° C. The respective peptides were separated by Microbore reverse-phase HPLC as described above. Several of the resolved peptides as well as the U937 92-kDa proenzyme and PMC-activated 84 kDa species which were transferred to PVDF membrane by electroblotting [Matsudaira, *J. Biol. Chem.* 262, 10035-10038 (1987)]were sequenced using an Applied Biosystems 470A gas phase sequencer [Grant et al., *J. Biol. Chem.* 262, 5886-5889 (1987)].

Enzyme Assays

Samples of purified 92-kDa U937 proenzyme in 0.05 M Tris-HCl, pH 7.5, containing 0.005 M $CaCl_2$, 0.05 M NaCl, and 0.01% Brij-35 were activated by the addition of 0.01 M stock solutions of the organomercurial compounds, p-aminophenylmercuric acetate (APMA) or phenylmercuric chloride (PMC) dissolved in 0.05 N NaOH to a final concentration of 0.5 mM for up to 16 hours at 37° C. Enzyme activity against $^{14}C$-gelatin (40,000 cpm/mg), murine EHS and human placental type IV collagen, and placental type V collagen was determined by conventional methodology as described by Wilhelm et al., *Proc. Natl. Acad. Sci. USA* 84, 6725–6729 (1987) and Collier et al., *J. Biol. Chem.* 263, 6579–6587 (1988).

For endoglycosidase assays, samples of purified 92-kDa type IV collagenase (2 μg) were dried in a speed-vac (Savant), redissolved in 0.5% $NaDodSO_4$ and 1.0% betamercaptoethanol, and diluted 5-fold into either N-glycanase (Genzyme) incubation buffer [0.2 M sodium phosphate, pH 8.6, 10 mM 1,10-phenanthroline, 1.25% NP-40 (Nonidet P-40 nonionic detergent, Sigma) or 0-glycanase (Genzyme) buffer (0.2 M Tris-maleate, pH 6.0, 0.01M D-galacton-lactone, 1.25% NP-40) and treated with either 10 units/ml of N-glycanase or 40 units/ml or 0-glycanase for 16 h at 37° C. Endoglycosidase H digestion was performed by methodology as described by Wilhelm et al., *Proc. Natl. Acad. Sci.* 83, 3756–3760 (1986). Samples were diluted with $NaDodSO_4$-sample buffer and subjected to Western blot analysis.

cDNA Cloning and Hybridization Conditions

Poly-A containing RNA was isolated from TPA-differentiated U-937 cells and TPA-treated HT-1080 cells [Sperling et al., *Mol. Cell. Biol.* 5, 569–575 (1985)]. The cDNA libraries using these RNAs were constructed by conventional techniques as described previously by Goldberg et al., *J. Biol. Chem.* 261, 6600–6605 (1986). The libraries were screened using a $^{32}P$ kinased ON2209 probe (see FIG. 1) to hybridize colonies replicated onto Zeta Probe (Bio-Rad) filters. In vitro translation, oligonucleotide synthesis, Northern blot analysis, and hybridization were performed by conventional methodology essentially as described for human fibroblast interstitial collagenase [Goldberg et al., supra., human type IV collagenase [Collier et al., *J. Biol. Chem.* 263, 6579–6587 (1988)], and human stromelysin [Wilhelm et al., *Proc. Natl. Acad. Sci. USA* 84, 6725–6729 (1987), without significant modification.

The results of the above laboratory preparative work leading to the complete primary structure and biological activity of the 92-kDa type IV collagenase are shown in FIGS. 1 to 10 of the accompanying drawings as further described in detail below.

RESULTS

SV-40 transformed human lung fibroblasts and HT1080 fibrosarcoma cells secrete a 92-kDa type IV collagenase identical to that found in macrophages and phorbol ester differentiated U-937 cells.

Figure 1:
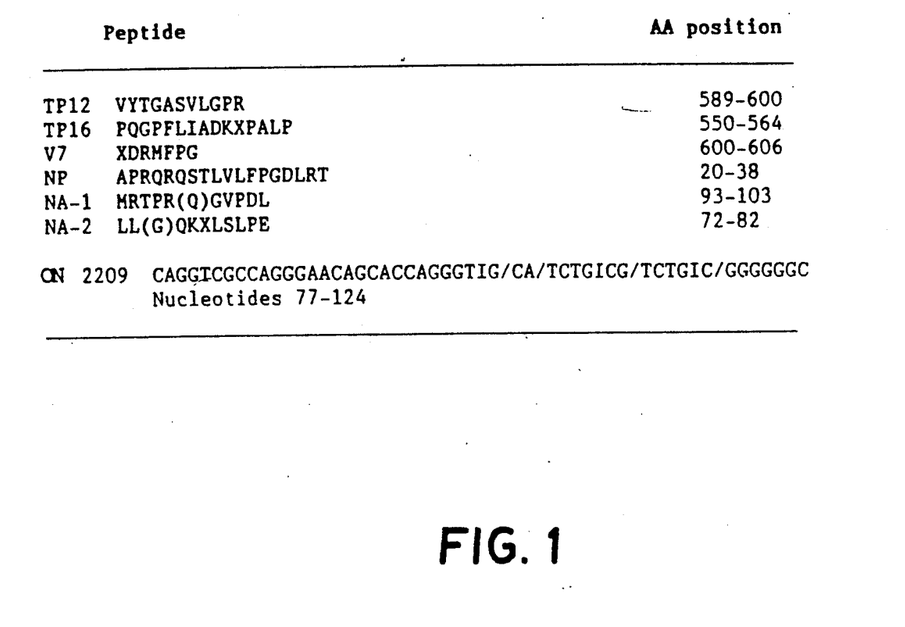
FIG. 1 shows the amino acid sequence of peptides derived from 92-kDa human type IV collagenase. Tryptic (TP) peptide and V7 (V) peptide from V-8 protease digest were fractioned and sequenced as described hereinafter under "Materials and Methods." Purified type IV procollagenase (NP) or PMC-activated enzyme (NA-1 and NA-2) were electro-blotted onto a PVDF membrane and subjected to NH$_2$-terminal sequence analysis. ON 2209 oligonucleotide probe was synthesized using the NH$_2$-terminal sequence of NP. The numbers represent the positions of the amino acid residues and the nucleotides in the sequence presented in FIG. 3.
Figure 2:
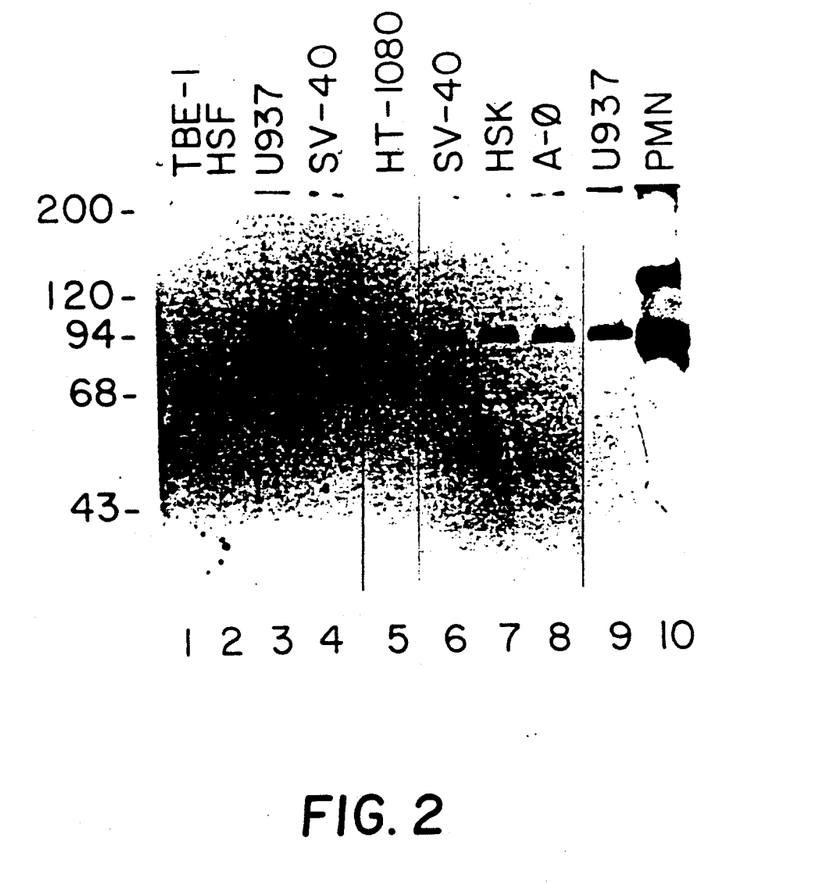
FIG. 2 shows the immunoblot analysis of 92 kDa type IV collagenases secreted by normal and transformed cels. Samples of purified type IV collagenase (100 ng) and serum-free conditioned medium (200 µl) were subjected to immunoblot analysis (unreduced). Lanes 1 and 2 are purified 72-kDa TBE-1 and human skin fibroblast type IV collagenase. Lanes 3 and 9 are purified and crude U-937 92-kDa type IV collagenase. Lanes 4 and 6 are purified and crude SV-40 92-kDa type IV collagenase. Lanes 5, 7, 8, and 10 represent samples of conditioned medium from HT-1080 cells, human skin keratinocytes (HSK), aleveolar macrophages (A-ϕ) and polymorphonuclear leukocytes (PMN), respectively.
Figure 3B:
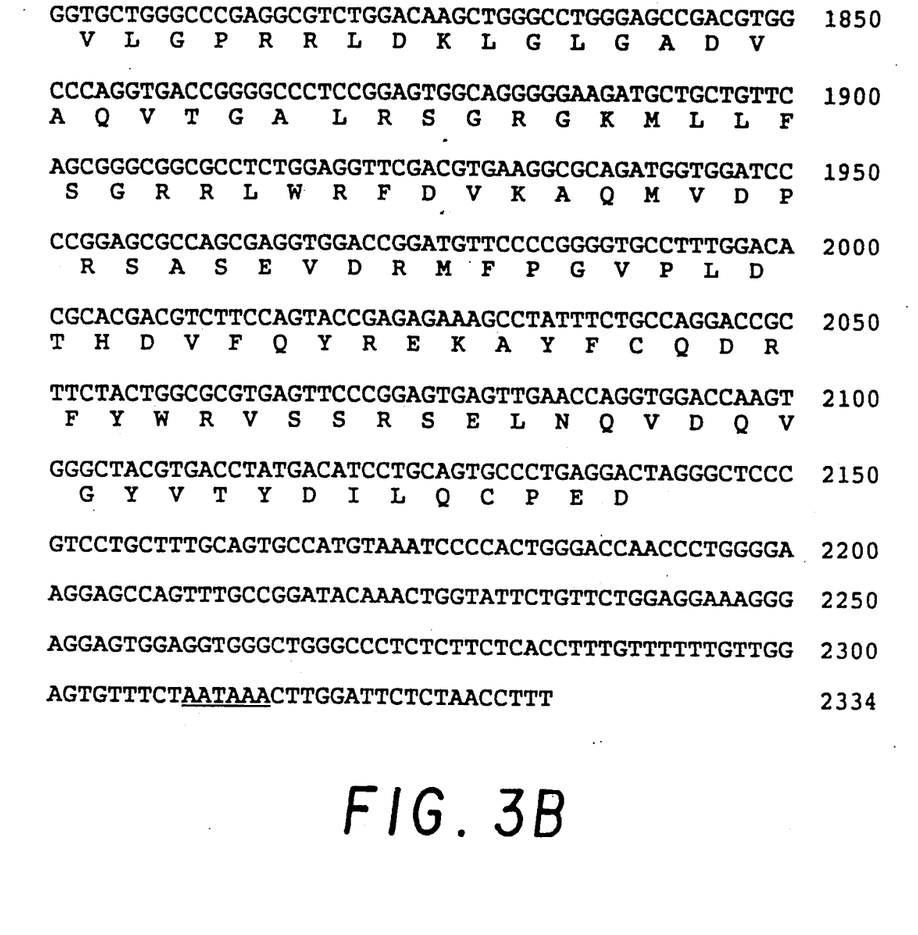

The present inventors have disclosed previously in copending application Ser. No. 07/93,421, filed Sept. 4, 1987, that human bronchial epithelial cells secrete a 72-kDa type IV collagenase in response to transformation with H-Ras. See also Collier et al., *J. Biol. Chem.* 263, 6579–6587 (1988). SV-40 transformed human lung fibroblasts secrete an additional gelatinolytic enzyme of 92-kDa which was not detected in the parental cell line. This enzyme has been purified as described herein from SV-40 transformed fetal lung fibroblasts, and the gelatinolytic metalloprotease of identical $M_r$ from the conditioned medium of TPA-differentiated U937 cells. To determine the primary structure, and confirm the relationship of the 92-kDa proteases from different sources, a monospecific antiserum was raised and partial amino acid sequence data was obtained for the 92-kDa enzyme. A preparation of U-937 92-kDa enzyme was electroblotted from $NaDodSO_4$-PAGE onto a filter support (see Methods) and subjected to $NH_2$-terminal sequence analysis. Another aliquot of the same preparation was further purified by Microbore reverse phase HPLC, and subjected to cleavage by trypsin and V-8 protease The peptides were separated on the same HPLC column and subjected to sequence analysis The $NH_2$-terminal sequence and the amino acid sequence of three internal peptides from the 92-kDa proenzyme are shown in FIG. 1. The $NH_2$-terminal sequence of the 92-kDa enzyme purified form the conditioned medium of SV-40 transformed human lung fibroblasts was determined in a similar manner and found to be identical to that of the enzyme secreted by U-937 cells (shown in FIG. 1). In addition, immunoblot analysis (FIG. 2) demonstrated that the rabbit antibody raised against the enzyme purified from U-937 cells recognized the 92-kDa enzyme secreted by TPA-stimulated SV-40 transformed lung fibroblasts, HT-1080 cells, alveolar macrophages and PMNs but not the 72-kDa type IV collagenase purified from H-Ras transformed bronchial epithelial cells or human skin fibroblasts.

The amino-terminal sequence of the proenzyme was reverse translated to generate an oligonucleotide probe (FIG. 1) which was used to screen a cDNA library constructed from mRNA isolated from TPA-treated HT1080 cells. The plasmid cDNA library was constructed and screened with the oligonucleotide probe as described previously by Goldberg et al., *J. Biol. Chem.* 261, 6600–6605 (1986). Twelve cDNA clones were isolated and the nucleotide sequence of the cDNA insert in the clone p92174.1 is presented in FIG. 3. The insert contains 2334 bp, excluding the poly AT and the poly GC tails and represents the mRNA encoding the 92-kDa preproenzyme. The sequence contains a 19 bp 5′ untranslated region followed by an AUG initiating methionine codon and an open reading frame with coding capacity for 707 amino acid long preproenzyme of predicted $M_4 = 78,426$. The 193 nucleotides long 3′ untranslated region contains the putative poly A addition site 19 bases upstream from the 3′ end of the RNA. The first 19 amino acids of the predicted sequence constitute a hydrophobic signal peptide followed by the start of the mature secreted protein at APRQR, as determined by amino acid sequence analysis (see FIG. 1).

Figure 4:
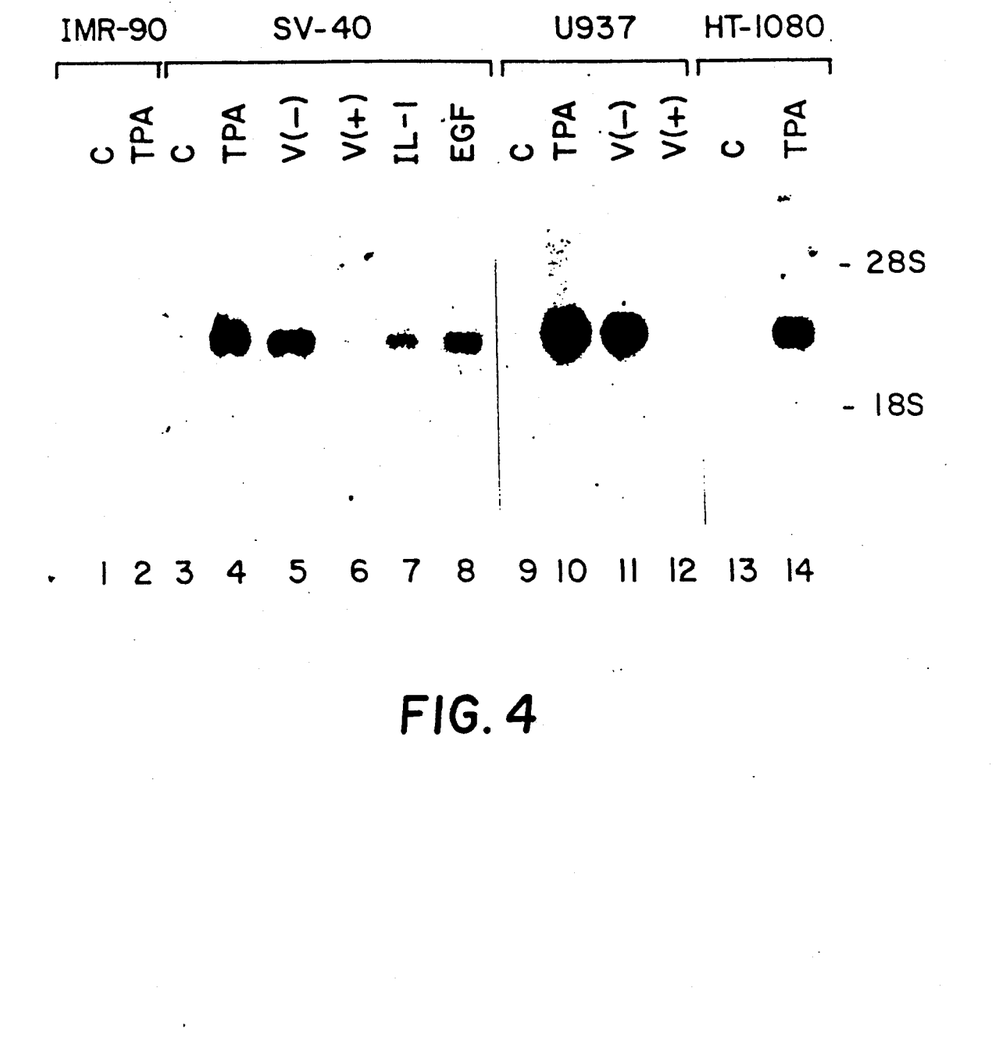
Figure 5:
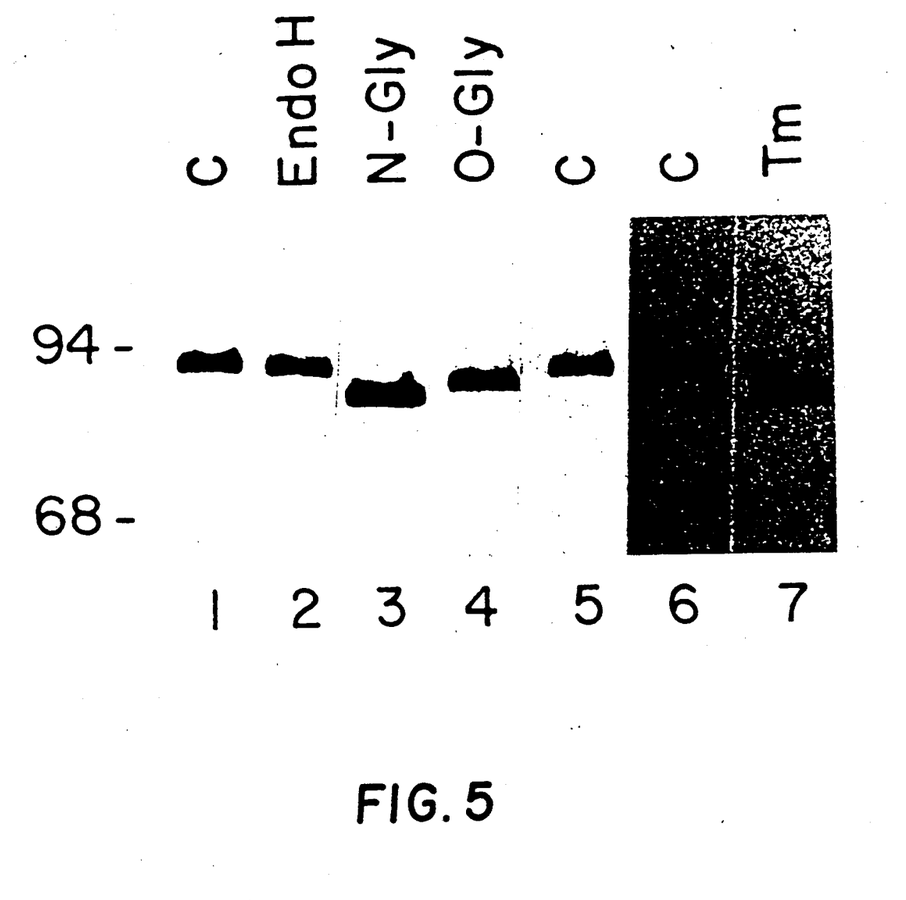

The sequences of peptides TP12, TP16, and V7 obtained from the enzyme secreted by the U-937 cells are present in the deduced amino acid sequence of the clone p92174.1 isolate from the HT-1080 cell cDNA library. The cDNA clone hybridizes to a 2.8 kb message in TPA-treated U-937 cells, HT-1080 and SV-40 transformed lung fibroblasts (FIG. 4). These data indicate that the 92-kDa metalloprotease secreted from TPA-differentiated U-937 cells is identical to the enzyme secreted by HT-1080 fibrosarcoma cells and SV-40 transformed human lung fibroblasts and in all likelihood is identical to the 92-kDa enzyme secreted by alveolar macrophages, PMNs [Hibbs et al., *J. Biol. Chem.* 260, 2493-2500 (1985); Hibbs et al., *J. Clin. Invest.* 80, 1644-1650 (1987)]and keratinocytes. Based on the similarity of the enzymatic properties and structural homology of this enzyme and the 72-kDa type IV collagenase described previously, this enzyme is referred to herein as 92-kDa type IV collagenase.

The apparent discrepancy between the predicted molecular weight and the molecular weight of the secreted protein determined by NaDodSO$_4$-PAGE is due to a post-translational modification of the enzyme through addition of several oligosaccharide side chains. The results presented in FIG. 5 demonstrate that treatment of the U-937 metalloprotease with N- or 0-glycanase but not endoglycosidase H leads to a reduction in molecular weight, indicating that the mature secreted 92-kDa proenzyme contains both O-linked and complex N-linked carbohydrates. The reduced $M_r$ of the enzyme after removal of carbohydrates is consistent with the $M_r$ 81,000 of the cell-free translation product synthesized using either the U-937 or HT-1080 mRNA data not shown). In agreement with this result, three potential N-linked glycosylation sites are found in the predicted amino acid sequence of the 92-kDa metalloprotease at positions 38, 120, and 127. Only one of these sites at Asn 120 is conserved in both interstitial collagenase and stromelysin.

92-kDa type IV collagenase consists of five distinct domains and is a member of the secreted ECM metalloprotease gene family.

Figure 6:
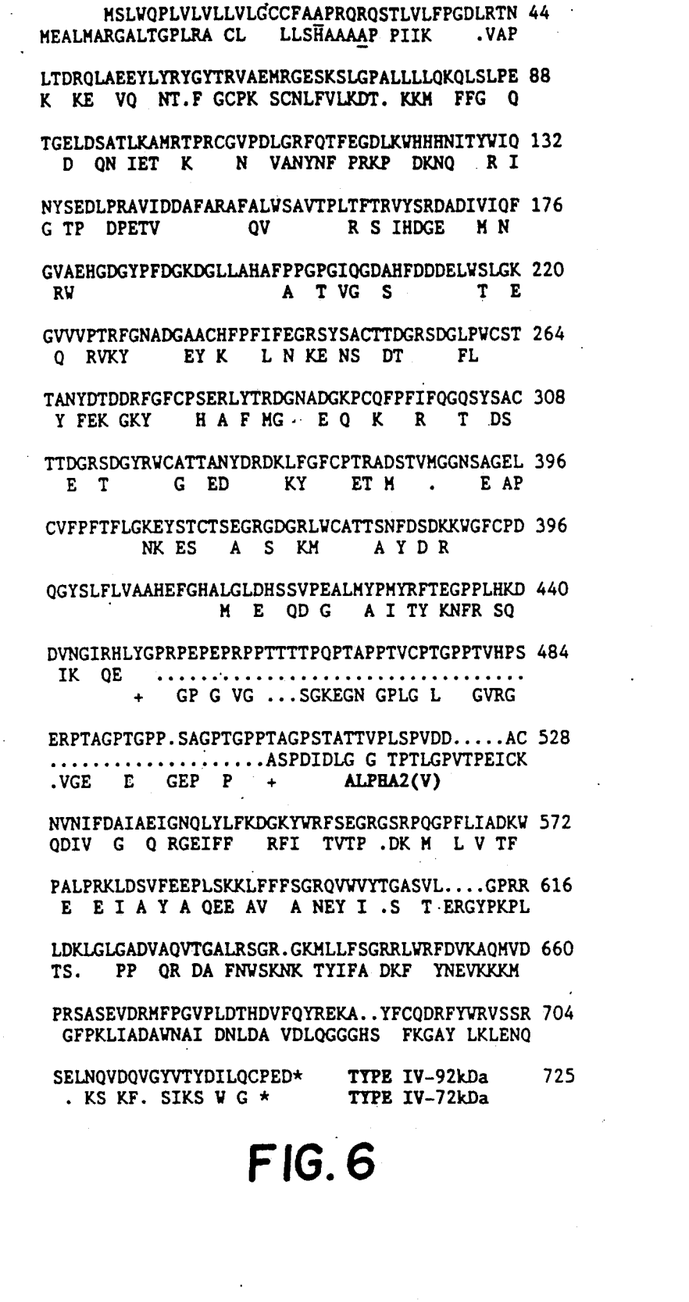
Figure 7:
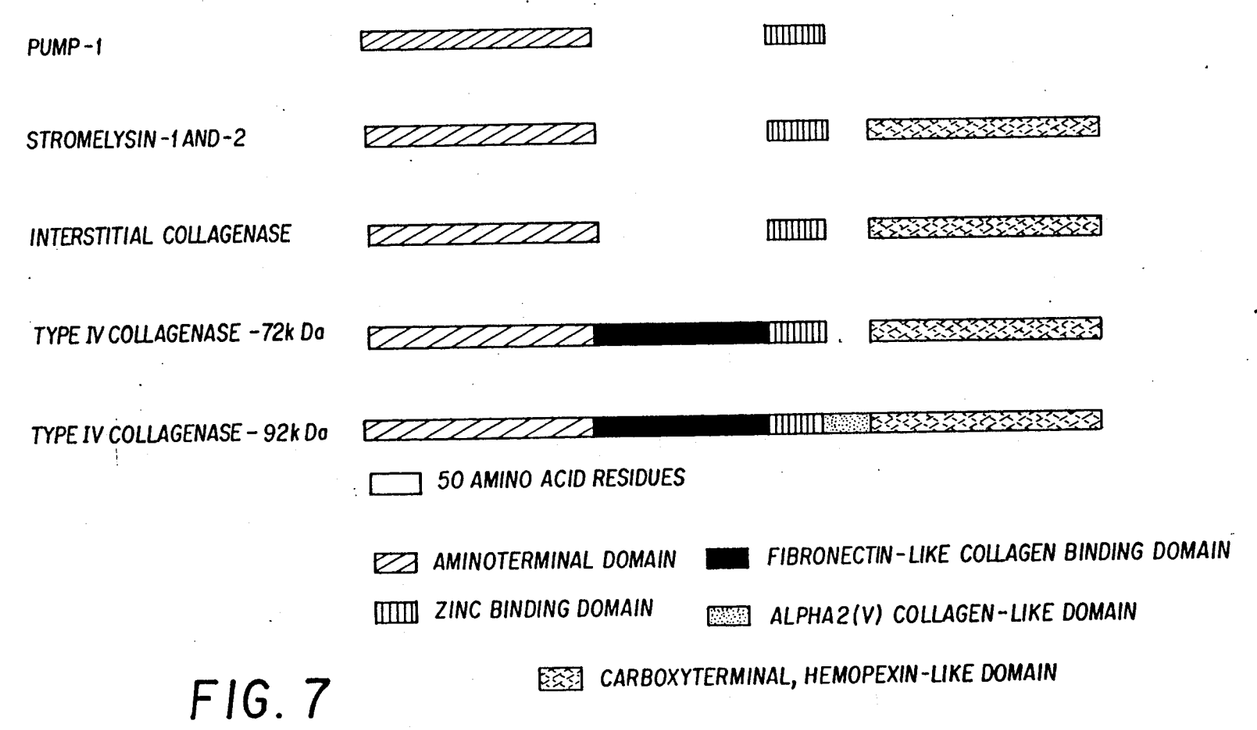

A comparison of the primary structure of 92-kDa and 72-kDa type IV collagenases presented in FIG. 6 demonstrates that the 92-kDa type IV collagenase consists of five domains. The amino-terminal domain, fibronectin-like collagen binding domain adjacent to the Zn binding domain [Collier et al., *J. Biol. Chem.* 263, 6579-6587 (1988) and hemopexin-like carboxyl end proximal domain [Muller et al., *Biochem. J.* 253, 187-192 (1988)]are homologous to those found in the 72-kDa type IV collagenase. In addition, the 92 TM kDa type collagenase contains a 54 amino acid long proline rich collagen-like domain of unknown function which is not found in the other members of the secreted ECM metalloprotease gene family (FIG. 7). The homology of this domain with a portion of the helical region of the alpha2(V) collagen [Weil et al., *Nuc. Acids Rec.* 15. 181-198 (1987)]is shown in FIG. 6. The size of this domain corresponds to a three fold multiple of the basic exon unit of the 54 bp typically found in the collagen genes (Yamada et al., *Cell* 22, 888-892 (1980)]. Both the sequence homology and the length of the insertion suggest that the appearance of this domain in the 92-kDa type IV collagenase is the result of a recombinational event between the enzyme precursor gene and a collagen gene.

The expression of the 92-kDa type IV collagenase can be induced by C-kinase activators and growth factors.

Phorbol esters (TPA), and indolactam V (−), both potent C-kinase activators Castagna et al., *J. Biol. Chem.* 257, 7847-7851 (1982); Fujiki et al., *Proc. Japan Acad.* 61(Ser.B), 45–47 (1985)]induce expression of the 92-kDa type IV collagenase (FIG. 4) in cultures of U-937 cells, SV-40 transformed fetal lung fibroblasts, and HT-1080 cells, but not in the parental fetal lung fibroblast cell line IMR-90. Those agents do not induce expression of the 72-kDa type IV collagenase. The inactive diastereoisomer indolactam V (+) had little if any effect on expression of the 92-kDa enzyme in these cell lines. The growth factors EGF and interleukin-1 induced a steady state level of the 92-kDa enzyme specific mRNA (FIG. 4) in SV-40 transformed cells.

The 92-kDa type IV collagenase proenzyme exists in a non-covalent complex with TIMP, which is activatable by APMA, yielding an enzyme with a substrate specificity profile identical to that of the 72-kDa type IV collagenase.

Figure 8:
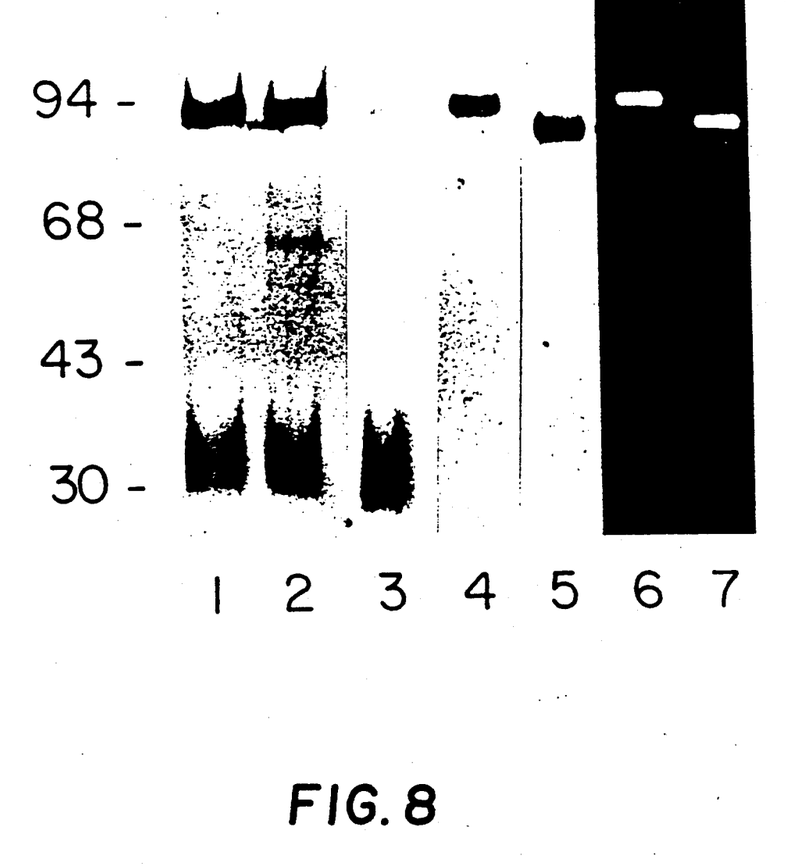
Figure 9A:
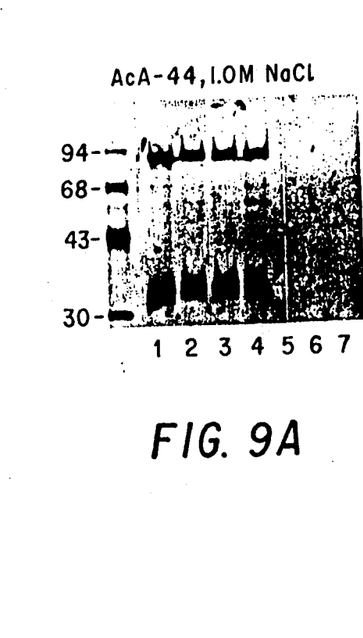
FIG. 9 shows that 92-kDa type IV procollagenase forms a non-covalent complex with TIMP. A purified preparation of the 92-kDa type IV collagenase was subjected to chromatography as indicated. Fractions were electrophoresed on either 10% (A and C) or 13% (B) NaDodSO$_4$-PAGE and stained with silver.
Figure 9B:
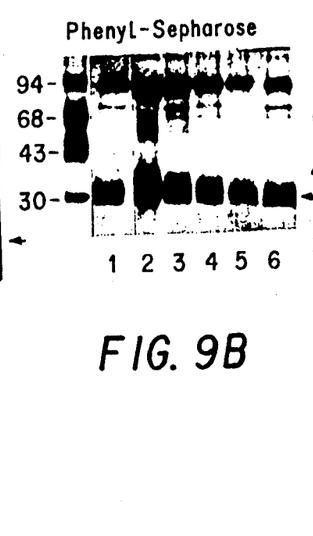
Figure 9C:
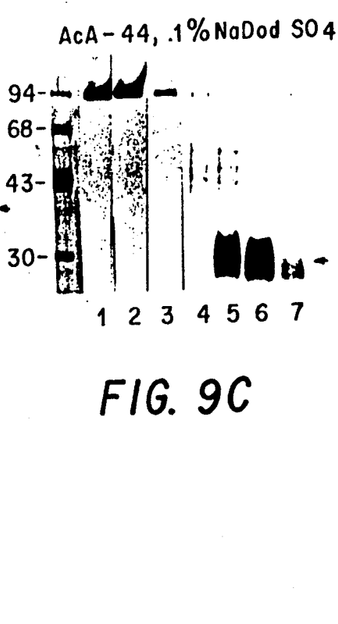
Figure 10:
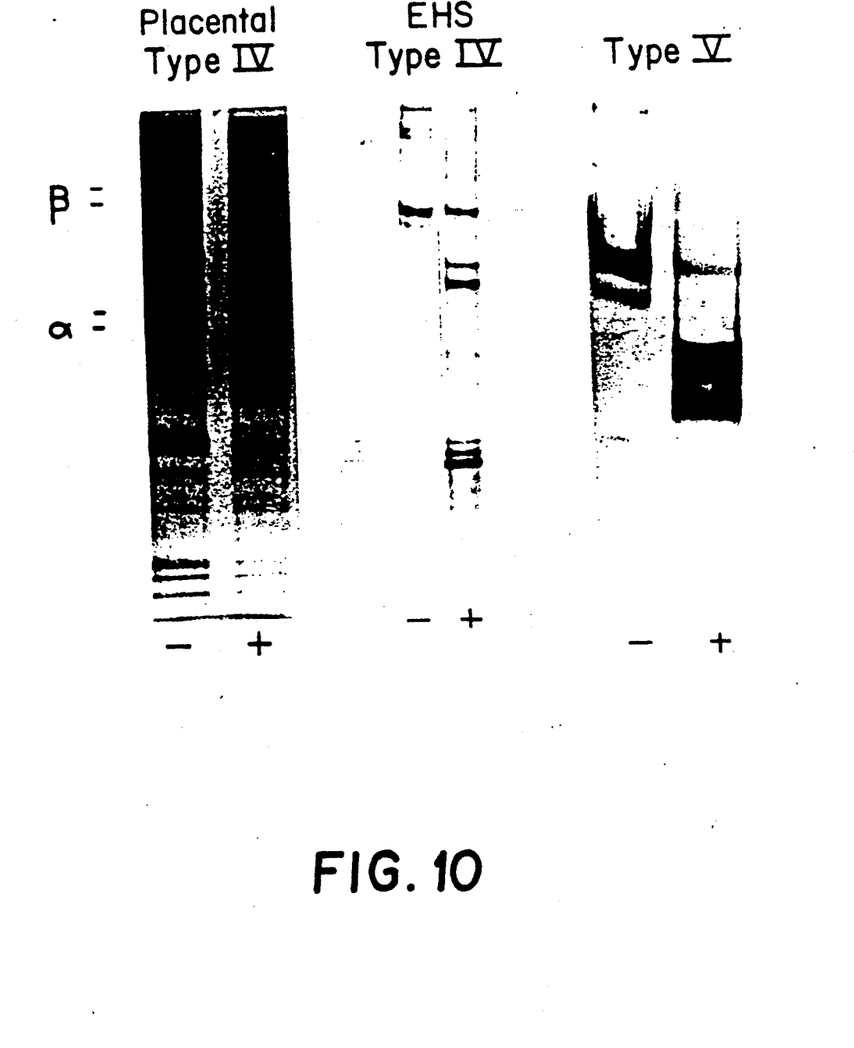
FIG. 10 shows that activated 92-kDa type IV procollagenase digests both pepsinized placental and mouse EHS type IV collagen as well as placental type V collagen at 32° C. Substrates (2 µg) were digested with the 92-kDa enzyme at 1:10 w/w ratio for 6 h at 37° C. and the digestion products analyzed by NaDodSO$_4$-PAGE and silver stained.

As shown in FIG. 8, silver starining of NaDodSO$_4$-PAGE purified preparations of 92-kDa type IV collagenase secreted by either U-937 (lane 1) or SV-40 transformed cells (lane 2) reveals the presence of a 30-kDa protein. This protein was identified as TIMP by Western blot analysis (FIG. 8, lane 3). Gel filtration chromatography of the gelatin-Sepnarose purified enzyme (FIG. 9) in either 1.0 M NaCl (FIG. 9A) or 2.0 M urea (date not shown) failed to separate the putative complex between these two proteins. Hydrophobic interaction chromatography on phenyl-Sepharose (FIG. 9B) was also unsuccessful. However, gel-filtration in the presence of 0.1% NaDodSO$_4$ did resolve the proenzyme and TIMP proteins (FIG. 9C). These data indicates that the 92-kDa purified zymogen and TIMP exist in a very stable non-covalent complex. These data are in agreement with results demonstrating that TIMP is co-immuno-precipitated with the 92-kDa proenzyme using a monospecific antibody directed against the 92-kDa protein which does not recognize TIMP. These findings demonstrate that the enzyme isolated from any cell type that secretes significant amounts of TIMP may be found in the form of a proenzyme-inhibitor complex.

The formation of a complex between TIMP and the 92-kDa proenzyme did not prevent its activation by treatment with the organomercurial PMC (FIG. 8). Autoactivation initiated by PMC [Grant et al., *J. Biol. Chem.* 262, 5886-5889 (1987)]resulted in a loss of 8-kDa determined by NaDodSO$_4$-PAGE (FIG. 8, lanes 5 and 7) but did not disrupt the enzyme-inhibitor complex. Amino-terminal sequence analysis of the 84-kDa PMC-activated enzyme revealed a mixed NH$_2$-terminal sequence. The sequence MRTPRCG was consistent with the cleavage of 73 amino acid residues from the NH$_2$-terminus of the proenzyme during organomercurial activation. In addition, the presence of the minor sequence LL(G)QKSL defined a possible intermediate species, with the NH$_2$-terminus starting 20 amino acid residues upstream from the 84-kDa activated enzyme. The latter two species were not resolved by NaDod-SO$_4$-PAGE.

The specific activity of the PMC-activated enzyme against $^{14}$C-gelatin was between 900 and 1200 units/mg of enzyme protein. The activated enzyme has no activity on type I collagen, proteoglycan, laminin, or fibronectin, but is capable of degrading native types IV and V collagen (FIG. 10) at 32° C. The cleavage products appeared to be identical to those generated by the 72-kDa type IV collagenase, as well as purified rabbit bone gelatinase [Murphy et al., *Biochim. Biophys. Acta* 831, 49-58 (1985)]and PMN 92-kDa gelatinase [Hibbs et al., *J. Biol. Chem.* 260, 2493-2500 (1985)]. The 72 kDa type IV procollagenase also forms a complex with an inhibitor (data not shown). Analysis of substrate specificity of the 72-kDa type IV collagenase and the 92-kDa enzyme will need to be reassessed when the enzymes free of the inhibitor complex become available. Recombinant enzyme isolated from a cell line which does not express TIMP is the most likely candidate as a source of such preparation because all the cells secreting the enzyme constitutively, also secrete TIMP.

Various other examples will be apparent to the person skilled in the art after reading the present disclosure without departing from the spirit and scope of the invention. It is intended that all such further examples be included within the scope of the appended claims.

What is claimed is:

1. The isolated cDNA comprising the 2335 base pair nucleotide sequence shown in FIG. 3 which encodes a 92-kDA type IV collagenase.

* * * * *